US012091713B2

(12) United States Patent
Skinner et al.

(10) Patent No.: US 12,091,713 B2
(45) Date of Patent: Sep. 17, 2024

(54) GENERALIZED STOCHASTIC SUPER-RESOLUTION SEQUENCING

(71) Applicants: ILLUMINA CAMBRIDGE LIMITED, Cambridge (GB); ILLUMINA, INC., San Diego, CA (US)

(72) Inventors: Gary Mark Skinner, Kedington (GB); Geraint Wyn Evans, Morriston (GB); Stanley S. Hong, Palo Alto, CA (US)

(73) Assignees: ILLUMINA CAMBRIDGE LIMITED, Cambridge (GB); ILLUMINA, INC., San Diego, CA (US)

( * ) Notice: Subject to any disclaimer, the term of this patent is extended or adjusted under 35 U.S.C. 154(b) by 386 days.

(21) Appl. No.: 17/395,294

(22) Filed: Aug. 5, 2021

(65) Prior Publication Data

US 2021/0363578 A1 Nov. 25, 2021

Related U.S. Application Data

(62) Division of application No. 16/294,696, filed on Mar. 6, 2019, now Pat. No. 11,111,533.

(60) Provisional application No. 62/640,909, filed on Mar. 9, 2018.

(51) Int. Cl.
*C12Q 1/6869* (2018.01)
*G01N 21/64* (2006.01)

(52) U.S. Cl.
CPC ....... *C12Q 1/6869* (2013.01); *G01N 21/6428* (2013.01); *G01N 2021/6439* (2013.01)

(58) Field of Classification Search
CPC ............ C12Q 1/6869; C12Q 2535/122; G01N 21/6428; G01N 2021/6439; G01N 21/6408; G01N 21/6452; G01N 2021/6432; G01N 2021/6441; G01N 21/6458
See application file for complete search history.

(56) References Cited

U.S. PATENT DOCUMENTS

| | | |
|---|---|---|
| 2005/0244870 A1 | 11/2005 | Chee et al. |
| 2006/0240439 A1 | 10/2006 | Smith et al. |
| 2009/0026082 A1 | 1/2009 | Rothberg et al. |
| 2009/0127259 A1 | 5/2009 | Rothberg et al. |
| 2010/0092957 A1 | 4/2010 | Zhao et al. |
| 2010/0137143 A1 | 6/2010 | Rothberg et al. |
| 2010/0282617 A1 | 11/2010 | Rothberg et al. |
| 2016/0168632 A1 | 6/2016 | Edwards et al. |
| 2018/0088048 A1 | 3/2018 | Dong et al. |

FOREIGN PATENT DOCUMENTS

| | | |
|---|---|---|
| JP | 7143341 B2 | 9/2022 |
| RU | 2611207 | 3/2016 |
| WO | WO 1991/006678 | 5/1991 |
| WO | WO 1998/059066 | 12/1998 |
| WO | WO 2013/112999 | 8/2013 |
| WO | WO 2016/065300 | 4/2016 |
| WO | WO 2017/087823 | 5/2017 |

OTHER PUBLICATIONS

Hell et al, The 2015 super-resolution microscopy roadmap, 2015, J. Phys. D: Appl. Phys. 48, pp. 1-35 (Year: 2015).*
Notice of Reasons for Refusal dated Sep. 5, 2023 for Japanese Application No. 2022-145883.
Bates, et al., "Multicolor Super-Resolution Imaging with Photo-Switchable Fluorescent Probes," Science 317, 2007, 1749-1753, 6 pages.
Haugland, "Molecular Probes Handbook," 6th Edition, Eugene, OR, USA, Updated Jan. 18, 2004, 110 pages.
Lakowicz, Jr., "Principles of Fluorescent Scpectroscopy, 2nd Edition," Kluwer Academic/Plenum Publishers: New York, NY, 1999, 707 pages.
Nienhaus, K. et al, "Where do we stand with super-resolution optical microscopy?" Journal of Molecular Biology (2016) 428(2), 308-322, 15 pages.
Schnitzbauer, et al., "Super-resolution microscopy with DNA-PAINT," Protocol, 2017, 1198-1228, 31 pages.
The Synthegen Catalog, Houston, Texas, 2004, 2 pages.
International Search Report and Written Opinion dated Jun. 16, 2019 for International Application No. PCT/US2019/021013, filed Mar. 6, 2019.
Extended European Search Report dated Oct. 7, 2021 for European Application No. 19763850.5.

* cited by examiner

*Primary Examiner* — Narayan K Bhat
(74) *Attorney, Agent, or Firm* — Sheppard, Mullin, Richter & Hampton LLP (57) ABSTRACT

An imaging system includes: a sample container including a flowcell that includes a plurality of attachment elements at a plurality of sample locations, wherein a single DNA template molecule is attached to each of the attachment elements, and further wherein an average distance between adjacent attachment elements is less than Abbe's limit; and an imager positioned to image photo-switching occurring at the plurality of attachment elements by capturing on and off events in a plurality of color channels at the same time as the on and off events are occurring for the attached molecules when a stochastic photo-switching chemistry is applied to all of the attached molecules at the same time causing the attached molecules to fluoresce in the on and off events in up to four different colors.

10 Claims, 7 Drawing Sheets

GENERALIZED STOCHASTIC SUPER-RESOLUTION SEQUENCING

CROSS REFERENCE TO RELATED APPLICATIONS

This application is a divisional of U.S. patent application Ser. No. 16/294,696, entitled "GENERALIZED STOCHASTIC SUPER-RESOLUTION SEQUENCING", filed on Mar. 6, 2019, now U.S. Pat. No. 11,111,533, issued Sep. 7, 2021, which claims priority to U.S. Provisional Patent Application No. 62/640,909, entitled "GENERALIZED STOCHASTIC SUPER-RESOLUTION SEQUENCING", filed on Mar. 9, 2018. The specifications of which are disclosed herein by reference.

BACKGROUND

Numerous technologies in the field of biology, including those used in DNA sequencing, have benefited from improved imaging systems and techniques. Early approaches to DNA sequencing included the dideoxy chain termination method (i.e., Sanger sequencing) and the chemical degradation method (i.e., Maxam-Gilbert sequencing). A desire for a lower-cost and more rapid alternative to these techniques led to the development of an ensemble sequencing approach known as Sequencing by Synthesis (SBS). In this process, single template molecules are first chemically amplified to generate surface-bound "clusters" of molecules having the same sequence. Once the clusters are produced, sequencing begins whereby fluorescent nucleotides are added by a modified polymerase based on the sequence of the template. The clusters are then excited by a light source resulting in the emittance of a characteristic fluorescent signal to determine the base call. The dyes are then removed, along with a 3' chain terminator, and the cycle is repeated for the next base in the sequence.

SUMMARY

Various examples of the technologies disclosed herein provide methods and techniques for super-resolution sequencing. In one example, a system and method for sequencing a plurality of polynucleotides includes: attaching a single DNA template molecule to each of a plurality of attachment elements on a sample container, wherein the average distance between adjacent elements is less than Abbe's limit; applying a stochastic photo-switching chemistry to all of the molecules at the same time to cause the attached molecules to fluoresce in on and off events in up to four different colors by stochastic photo-switching; and imaging the on and off events in a color channel for each color in real-time as the on and off events are occurring for the attached molecules. The average distance between adjacent elements may be less than about 20 nm or it may be within a range of about 2 nm to about 20 nm.

In a further example, a method of sequencing polynucleotides may include: providing an array of nucleotide sequences anchored to a solid support, wherein the average distance between adjacent anchors is less than Abbe's limit; providing a mixture to the array comprising an enzyme capable of coupling nucleotides, a deblocking agent, a nucleic acid bound to a strand of nucleotides having a sequence complimentary to the nucleotide sequences anchored to the solid support, and more than one nucleotide analog comprising a base with a label moiety and corresponding quencher moiety bound thereto wherein the label moieties are correlated with a specific base moiety; and allowing sequential addition of a plurality of the nucleotide analogs to the nucleic acid to proceed via several reaction cycles in the mixture while concurrently imaging the label moieties within the array; wherein each reaction cycle may include: (i) the polymerase adding a nucleotide analog to the nucleic acid by cleaving the quencher moiety and forming a transient nucleic acid species comprising the label moiety; and (ii) the deblocking agent modifying the transient nucleic acid species to remove the label moiety. In some applications, the average distance between adjacent anchors is less than 20 nm. In further applications, the average distance between adjacent anchors is within a range of 2 nm to 20 nm. The enzyme capable of coupling nucleotides may include a polymerase, a myosin or a kinase.

The nucleotide analog may include a pentose moiety having a 3' carbon and the label moiety may be attached to the nucleotide at the 3' carbon. In another example, the nucleotide analog may include a triphosphate moiety and the quencher moiety may be attached to the triphosphate moiety.

In some applications, the deblocking agent may include a phosphoesterase enzyme (e.g., phosphodiesterase, phosphotriesterase, etc.). The phosphoesterase may be included to selectively remove a phosphodiester moiety or the phosphotriester moiety from the transient nucleic acid species. The phosphoesterase may be selected from the group consisting of Endonuclease IV and AP endonuclease.

As an example, the transient nucleic acid species may be present for at least 1 millisecond before the deblocking agent modifies the transient nucleic acid species to remove the label moiety. As a further example, the transient nucleic acid species may be present for no more than 30 seconds before the deblocking agent modifies the transient nucleic acid species to remove the label moiety.

In various applications, the several reaction cycles may include at least 100 reaction cycles, whereby the nucleic acid is extended by addition of at least 100 nucleotide analogs. In various applications, the enzyme capable of coupling nucleotides comprises a polymerase, a myosin, or a kinase.

In further examples, a method of sequencing a plurality of polynucleotides includes: attaching a single DNA template molecule to each of a plurality of attachment elements on a sample container, wherein the average distance between adjacent elements is less than Abbe's limit; applying a stochastic photo-switching chemistry to all of the molecules at the same time to cause the attached molecules to fluoresce in on and off events in up to four different colors by stochastic photo-switching; and imaging the on and off events in a color channel for each color in real-time as the on and off events are occurring for the attached molecules. Due to the stochastic nature of the photo switching, in various examples the probability that an on event for a given base for a given molecule will occur at the same time as an on event for the same base at a molecule adjacent to the given molecule is less than 0.5%. The concentrations of reagents for the stochastic photo-switching may be chosen such that the probability that an on event for a given base for a given molecule will occur at the same time as an on event for the same base at a molecule adjacent to the given molecule is less than 0.5%. In other examples, other concentrations may be used. The average distance between adjacent elements may be less than about 20 nm or it may be within a range of about 2 nm to about 20 nm. In some applications, each of the plurality of attachment elements on the sample container may be within a field of view of an imager used to image the on and off events such that imaging of the on and off events occurs at the same time for the attached molecules at the plurality of attachment elements. Applying a stochastic photo-switching chemistry to all of the attached molecules at the same time may include applying a stochastic optical reconstruction microscopy, a DNA Points Accumulation for Imaging in Nanoscale Topography, or a direct stochastic optical reconstruction microscopy stochastic photoswitching chemistry to all of the molecules at the same time.

The process may further include controlling a rate at which the on and off events occur to control a probability that an on event for a given base for a given molecule will occur at the same time as an on event for the same base at a molecule adjacent to the given molecule. In some applications, controlling the rate at which the on and off events occur may include adjusting concentrations of nucleotides and enzyme in the stochastic photo-switching chemistry. In other applications, controlling the rate at which the on and off events occur comprises adjusting the on and off times so that the probability that an on event for a given base for a given molecule will occur at the same time as an on event for the same base at a molecule adjacent to the given molecule is lower than a determined error rate in a sequencing application in which the method is applied.

In some applications, the process may further include determining whether an illumination intensity of a detected on event in a color channel is greater than a predetermined threshold. The process may also include determining whether a spot size of a detected on event in a color channel is greater than a predetermined threshold.

An imaging system may include a sample container comprising a plurality of attachment elements wherein a single DNA template molecule is attached to each of the attachment elements, and further wherein the average distance between adjacent attachment elements is less than Abbe's limit; and an imager positioned to image photo-switching occurring at the plurality of attachment elements by capturing on and off events in a plurality of color channels at the same time as the on and off events are occurring for the attached molecules when a stochastic photo-switching chemistry is applied to all of the attached molecules at the same time causing the attached molecules to fluoresce in the on and off events in up to four different colors. The sample container may include a flowcell that comprises the plurality of attachment elements at a plurality of sample locations. In various examples the average distance between adjacent elements is less than about 20 nm or it may be within a range of about 2 nm to about 20 nm. In various examples, each of the plurality of attachment elements on the sample container is within a field of view of the imager used to image the photo-switching such that the capturing of the on and off events occurs at the same time for the attached molecules at the plurality of attachment elements. The stochastic photo-switching chemistry applied to all of the attached molecules at the same time may include a stochastic optical reconstruction microscopy, a DNA Points Accumulation for Imaging in Nanoscale Topography, or a direct stochastic optical reconstruction microscopy stochastic photoswitching chemistry.

The imaging system may employ stochastic optical reconstruction microscopy, DNA Points Accumulation for Imaging in Nanoscale Topography or direct switching driven by photochemical reactions as the stochastic photo-switching chemistry applied to cause the attached molecules to fluoresce. The concentrations of reagents for the stochastic photo switching are such that the probability that an on event for a given base for a given molecule will occur at the same time as an on event for the same base at a molecule adjacent to the given molecule is less than 0.5%.

The imaging system may be implemented such that the rate at which the on and off events occur yields a probability that an on event for a given base for a given molecule will occur at the same time as an on event for the same base at a molecule adjacent to the given molecule is lower than a determined error rate in a sequencing application in which the method is applied. The imaging system may further determine whether an illumination intensity or a spot size of a detected on event in a color channel is greater than a predetermined threshold.

Other features and aspects of the disclosed technology will become apparent from the following detailed description, taken in conjunction with the accompanying drawings, which illustrate, by way of example, the features in accordance with implementations of the disclosed technology. The summary is not intended to limit the scope of any inventions described herein, which are defined by the claims and equivalents.

It should be appreciated that all combinations of the foregoing concepts (provided such concepts are not mutually inconsistent) are contemplated as being part of the inventive subject matter disclosed herein.

BRIEF DESCRIPTION OF THE DRAWINGS

The technology disclosed herein, in accordance with one or more examples, is described in detail with reference to the following figures. These figures are provided to facilitate the reader's understanding of the disclosed technology, and are not intended to be exhaustive or to limit the disclosure to the precise forms disclosed. Indeed, the drawings in the figures are provided for purposes of illustration only, and merely depict typical or example examples of the disclosed technology. Furthermore, it should be noted that for clarity and ease of illustration, the elements in the figures have not necessarily been drawn to scale.

It should be understood that the disclosed technology can be practiced with modification and alteration, and that the disclosed technology be limited only by the claims and the equivalents thereof.

DETAILED DESCRIPTION

Various examples disclosed herein provide a super-resolution sequencing using a homogenous, single-pot reaction in which a stochastic switching of fluorophores is coupled to the sequencing reaction itself and imaging occurs for multiple adjacent molecules in real time at the time of the incorporation. Particularly, in some applications, a sample container is provided with a plurality of wells, or attachment elements, disposed at a spacing that is less than the spacing otherwise permitted to allow resolving the individual elements under Abbe's limit. A single DNA template molecule is attached to each attachment element in the sample container for sequencing. A sequencing chemistry is applied that provides a stochastic photo-switching of all the molecules in a group of molecules being imaged. Imaging of the reactions takes place in real-time for all the molecules at the same time as the fluorophores switch on and off within the group. Because the reactions are stochastic and not synchronized among the molecules, there is a statistical probability that adjacent molecules will not incorporate the same base at the same time.

In some applications, sequencing occurs by a polymerase incorporating the correct nucleotide, and during the incorporation event, the fluorophore switches on for a short time and switches off again. The imaging occurs in real time at the time of the incorporation event. At the same time, incorporation events are happening at multiple attachment elements in the sample container. Because the switching at these various molecules is stochastic, and not synchronized between the molecules, they can all be imaged at the same time as the reactions are occurring, so that a sequential and more time-consuming process is not required.

Before describing various super-resolution processes in detail, it is useful to describe an example environment with which such processes can be implemented. One such example environment is that of an image scanning system, such as that illustrated in FIG. 1. The example image scanning system may include a device for obtaining or producing an image of a region. The example outlined in FIG. 1 shows an example imaging configuration of a backlight design.

Figure 1:
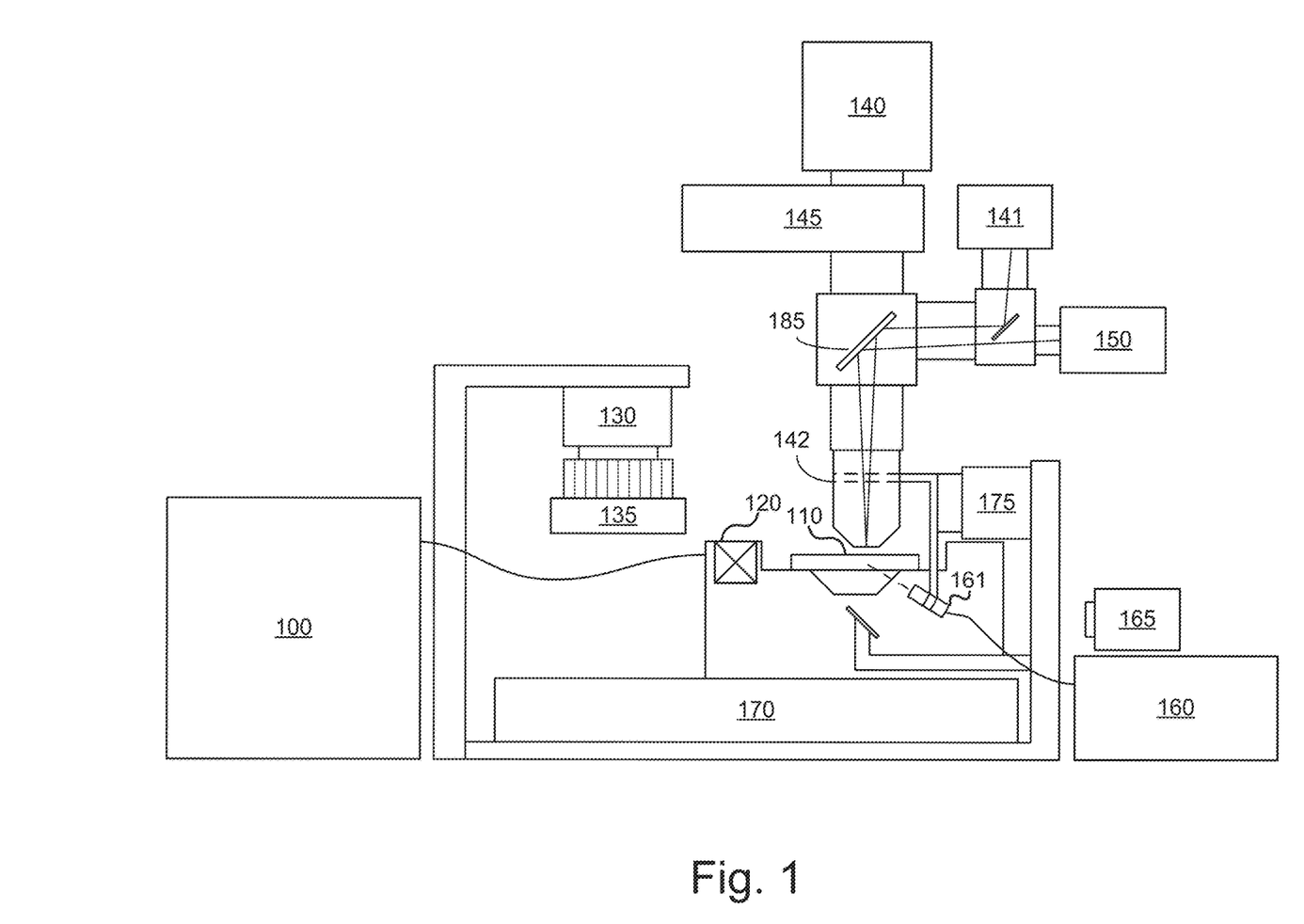
FIG. 1 illustrates a simplified block diagram of one example of an image scanning system with which systems and methods disclosed herein may be implemented.

As can be seen in the example of FIG. 1, subject samples are located on sample container 110, which is positioned on a sample stage 170 under an objective lens 142. Light source 160 and associated optics direct a beam of light, such as laser light, to a chosen sample location on the sample container 110. The sample fluoresces, and the resultant light is collected by the objective lens 142 and directed to a photo-detecting camera system 140 to detect the florescence. Sample stage 170 is moved relative to objective lens 142 to position the next sample location on sample container 110 at the focal point of the objective lens 142. Movement of sample container 110 relative to objective lens 142 can be achieved by moving the sample stage itself, the objective lens, the entire optical stage, or any combination of the foregoing. Further examples may also include moving the entire imaging system over a stationary sample.

Fluid delivery module or device 100 directs the flow of reagents (e.g., fluorescent nucleotides, buffers, enzymes, cleavage reagents, etc.) to (and through) sample container 110 and waste valve 120. In some applications, the sample container 110 can be implemented as a flowcell that includes clusters of nucleic acid sequences at a plurality of sample locations on the sample container 110. The samples to be sequenced may be attached to the substrate of the flowcell, along with other optional components.

The system also comprises temperature station actuator 130 and heater/cooler 135 that can optionally regulate the temperature of conditions of the fluids within the sample container 110. Camera system 140 can be included to monitor and track the sequencing of sample container 110. Camera system 140 can be implemented, for example, as a CCD camera, which can interact with various filters within filter switching assembly 145, objective lens 142, and focusing laser 150. Camera system 140 is not limited to a CCD camera, and other cameras and image sensor technologies can be used.

Light source 160 (e.g., an excitation laser within an assembly optionally comprising multiple lasers) or other light source can be included to illuminate fluorescent sequencing reactions within the samples via illumination through fiber optic interface 161 (which can optionally comprise one or more re-imaging lenses, a fiber optic mounting, etc.). Low watt lamp 165, focusing laser 150, focusing detector 141, and reverse dichroic 185 are also presented in the example shown. Focusing laser 150 may be used together with focusing detector 141 to auto-focus the system, i.e., by adjusting the distance between objective 142 and sample 110, or using other focusing techniques as known in the art. In some applications focusing laser 150 may be turned off during imaging. In other applications, an alternative focus configuration can include a second focusing camera (not shown), which can be a quadrant detector, a Position Sensitive Detector (PSD), or similar detector to measure the location of the scattered beam reflected from the surface concurrent with data collection.

Although illustrated as a backlit device, other examples may include a light from a laser or other light source (not shown) that is directed through the objective lens 142 onto the samples on sample container 110. Sample container 110 can be ultimately mounted on a sample stage 170 to provide movement and alignment of the sample container 110 relative to the objective lens 142. The sample stage can have one or more actuators to allow it to move in any of three directions. For example, in terms of the Cartesian coordinate system, actuators can be provided to allow the stage to move in the X, Y and Z directions relative to the objective lens. This can allow one or more sample locations on sample container 110 to be positioned in optical alignment with objective lens 142.

A focus (z-axis) component 175 is shown in this example as being included to control positioning of the optical components relative to the sample container 110 in the focus direction (typically referred to as the z axis, or z direction). Focus component 175 can include one or more actuators physically coupled to the optical stage or the sample stage, or both, to move sample container 110 on sample stage 170 relative to the optical components (e.g., the objective lens 142) to provide proper focusing for the imaging operation. For example, the actuator may be physically coupled to the respective stage such as, for example, by mechanical, magnetic, fluidic or other attachment or contact directly or indirectly to or with the stage. The one or more actuators can be configured to move the stage in the z-direction while maintaining the sample stage in the same plane (e.g., maintaining a level or horizontal attitude, perpendicular to the optical axis). The one or more actuators can also be configured to tilt the stage. This can be done, for example, so that sample container 110 can be leveled dynamically to account for any slope in its surfaces.

Focusing of the system generally may refer to aligning the focal plane of the objective lens with the sample to be imaged at the chosen sample location. However, focusing can also refer to adjustments to the system to obtain a desired characteristic for a representation of the sample such as, for example, a desired level of sharpness or contrast for an image of a test sample. Because the usable depth of field of the focal plane of the objective lens may be very small (sometimes on the order of 1 µm or less), focus component 175 closely follows the surface being imaged. Because the sample container is not perfectly flat as fixtured in the instrument, focus component 175 may be set up to follow this profile while moving along in the scanning direction (typically referred to as the y-axis herein).

The light emanating from a test sample at a sample location being imaged can be directed to one or more detectors, including, for example, camera system 140. Detectors can include, for example a CCD camera. An aperture can be included and positioned to allow only light emanating from the focus area to pass to the detector. The aperture can be included to improve image quality by filtering out components of the light that emanate from areas that are outside of the focus area. Emission filters can be included in filter switching assembly 145, which can be selected to record a determined emission wavelength and to cut out any stray laser light.

In various examples, sample container 110 can include one or more substrates upon which the samples are provided. For example, in the case of a system to analyze a large number of different nucleic acid sequences, sample container 110 can include one or more substrates on which nucleic acids to be sequenced are bound, attached or associated. In various examples, the substrate can include any inert substrate or matrix to which nucleic acids can be attached, such as for example glass surfaces, plastic surfaces, latex, dextran, polystyrene surfaces, polypropylene surfaces, polyacrylamide gels, gold surfaces, and silicon wafers. In some applications, the substrate is within a channel or other area at a plurality of locations formed in a matrix or array across the sample container 110.

One or more controllers (not illustrated) can be provided to control the operation of a scanning system, such as the example scanning system described above with reference to FIG. 1. The controller can be implemented to control aspects of system operation such as, for example, focusing, stage movement, and imaging operations. In various applications, the controller can be implemented using hardware, software, or a combination of the foregoing. For example, in some implementations the controller can include one or more CPUs or processors with associated memory. As another example, the controller can comprise hardware or other circuitry to control the operation. For example, this circuitry can include one or more of the following: field programmable gate array (FPGA), application specific integrated circuit (ASIC), programmable logic device (PLD), complex programmable logic device (CPLD), a programmable logic array (PLA), programmable array logic (PAL) or other similar processing device or circuitry. As yet another example, the controller can comprise a combination of this circuitry with one or more processors.

Sequencing technologies that can be used with systems such as that described with reference to FIG. 1 include next-generation sequencing (NGS) technologies. Sequencing by Synthesis (SBS) is a widely adopted NGS technology that uses modified dNTPs containing a terminator that blocks further polymerization. The sequencing reaction may be conducted simultaneously on a large number of template molecules. With SBS, a fluorescently labeled reversible terminator is imaged as each dNTP is added, and then cleaved to allow incorporation of the next base. Because all 4 reversible terminator-bound dNTPs are present during each sequencing cycle, natural competition minimizes incorporation bias. This results in a base-by-base sequencing that enables accurate data for a broad range of applications.

With NGS, DNA polymerase catalyzes the incorporation of fluorescently labeled deoxyribonucleotide triphosphates (dNTPs) into a DNA template strand during sequential cycles of DNA synthesis. During each cycle, at the point of incorporation, the nucleotides are identified by fluorophore excitation. One difference is that, instead of sequencing a single DNA fragment, NGS extends this process across millions of fragments in a massively parallel fashion.

One approach to NGS includes four basic steps: library preparation, cluster generation, sequencing, and data analysis. With library preparation, the sequencing library is prepared by random fragmentation of the DNA or cDNA sample, followed by 5' and 3' adapter ligation. Alternatively, the fragmentation and ligation reactions are combined into a single step that greatly increases the efficiency of the library preparation process. Adapter-ligated fragments are then PCR amplified and gel purified.

For cluster generation, the library is loaded into a flow cell where fragments are captured on a lawn of surface-bound oligos complementary to the library adapters. Each fragment is then amplified into distinct, clonal clusters through bridge amplification. When cluster generation is complete, the templates are ready for sequencing. One approach to SBS uses a reversible terminator-based method that detects single bases as they are incorporated into DNA template strands. As all four reversible terminator-bound dNTPs are present during each sequencing cycle, natural competition minimizes incorporation bias and reduces raw error rates compared to other technologies. During data analysis and alignment, the newly identified sequence reads are aligned to a reference genome. Following alignment, many variations of analysis are possible, such as single nucleotide polymorphism (SNP) or insertion-deletion (indel) identification, read counting for RNA methods, phylogenetic or metagenomic analysis, and more.

Important in imaging systems is the speed at which scanning operations can take place. Consider sequencing systems, for example. In such systems, it is often desirable to increase the speed with which sample molecules can be read. One way to increase the throughput of imaging systems is to decrease the size and spacing of the structures being imaged. In sequencing systems, this can be accomplished by packing template molecules closer together to increase the number of reads that can be accomplished for a given unit area. However, resolution of the imaging system is limited by the wavelength of light, aperture of the optics, and other factors.

In 1873 a German physicist by the name of Ernest Abbe published a formula defining the resolution limit of the microscope. Abbe's limit is defined as:

$$d = \frac{\lambda}{2NA}.$$

Where $\lambda$ is the wavelength of the light waves illuminating the specimen, or the excitation wavelength band in fluorescence. NA is the numerical aperture of the objective lens, which is defined by the refractive index of the transmission medium, n, multiplied by the sine of the aperture angle $(\sin(\alpha))$, where $\alpha$=half-angle of maximum cone of light that can enter or exit the lens. Accordingly, NA can be set forth as NA=n·sin($\alpha$), and Abbe's Limit can be rewritten as:

$$d = \frac{\lambda}{2n\sin\alpha}.$$

This resolution limit, often referred to as the diffraction barrier, defines the ability of the optical instrument to distinguish between two objects separated by a lateral distance less than approximately half the wavelength of light used to image the specimen. The 2014 Nobel Prize for chemistry was awarded for bypassing this scientific limitation. Indeed, Abbe's limit has now been overcome by a number of techniques. These include: STochastic Optical Reconstruction Microscopy (STORM), STimulated Emission Depletion Microscopy (STED), PhotoActivation Localization Microscopy (PALM) and Structured Illumination Microscopy (SIM). All of these methods allow resolutions to be achieved of much lower than 200 nm, down to ~20 nm for STORM, STED and PALM, and about 100 nm for SIM.

STORM, for example, relies on stochastic switching of single-molecule fluorescence so that only a small fraction of the fluorophores is activated stochastically at any given time. The activated fluorophores are separated sufficiently such that they can be resolved within Abbe's limit. This enables determining their positions with sufficient precision. However, often it involves the process be repeated and multiple images (snapshots) of the sample be taken, each capturing a random subset of the fluorophores, so that a final image can be reconstructed. The final image is generated by accumulating the multiple images. Accordingly, the activations are physically separated so that they can be optically resolved.

Although the systems and methods may be described herein from time to time in the context of this example system of FIG. 1, this is only one example with which these systems and methods might be implemented. The systems and methods described herein can be implemented with this and other scanners, microscopes and other imaging systems.

Figure 2:
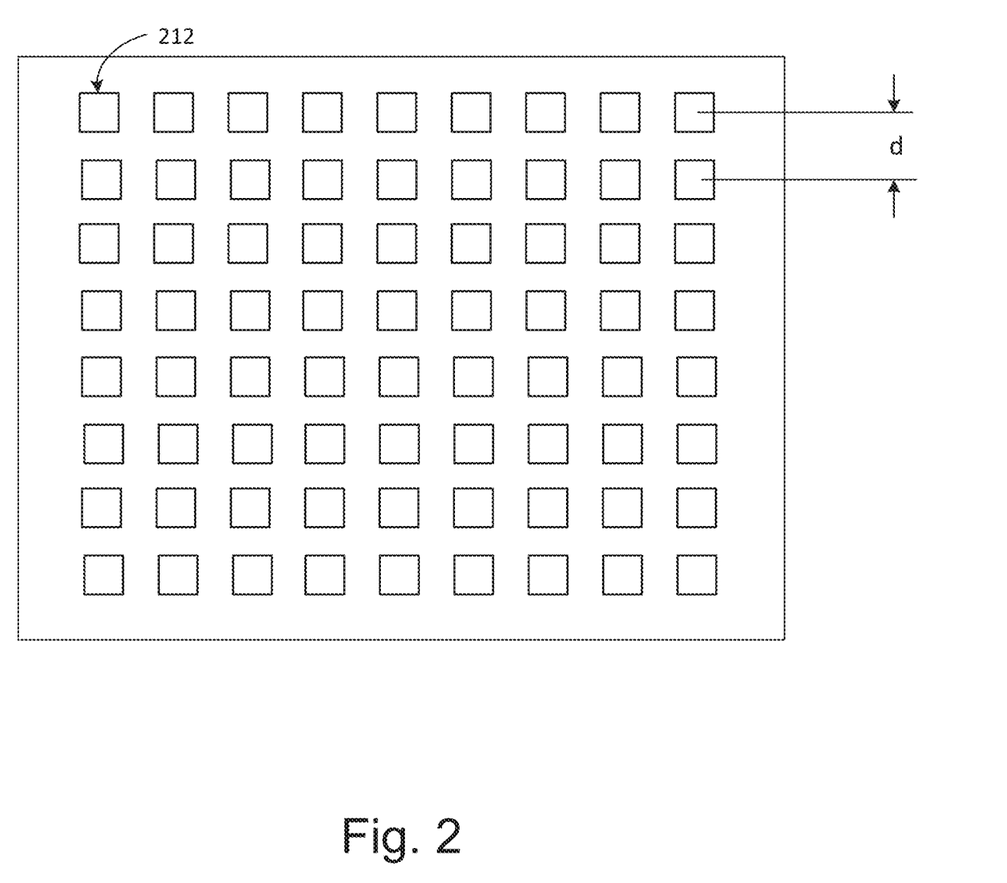
FIG. 2 illustrates an example of a sample container including a plurality of attachment points, or anchors.

The sample container for an imaging system may be constructed as an array of single-molecule attachment elements. An example container for single molecule stochastic sequencing is illustrated in FIG. 2. Such a container, with multiple rows of attachment elements 212 can allow several DNA molecules to be individually sequenced in parallel. However, the minimum spacing, d, of the attachment elements 212 in various applications can be limited by the optical resolution of the system. In some applications, the attachment elements 212 can include zero-mode waveguides, which are optical nanostructures that serve to confine the observation volume, thereby extending the concentrations for single-molecule microscopy.

Figure 3:
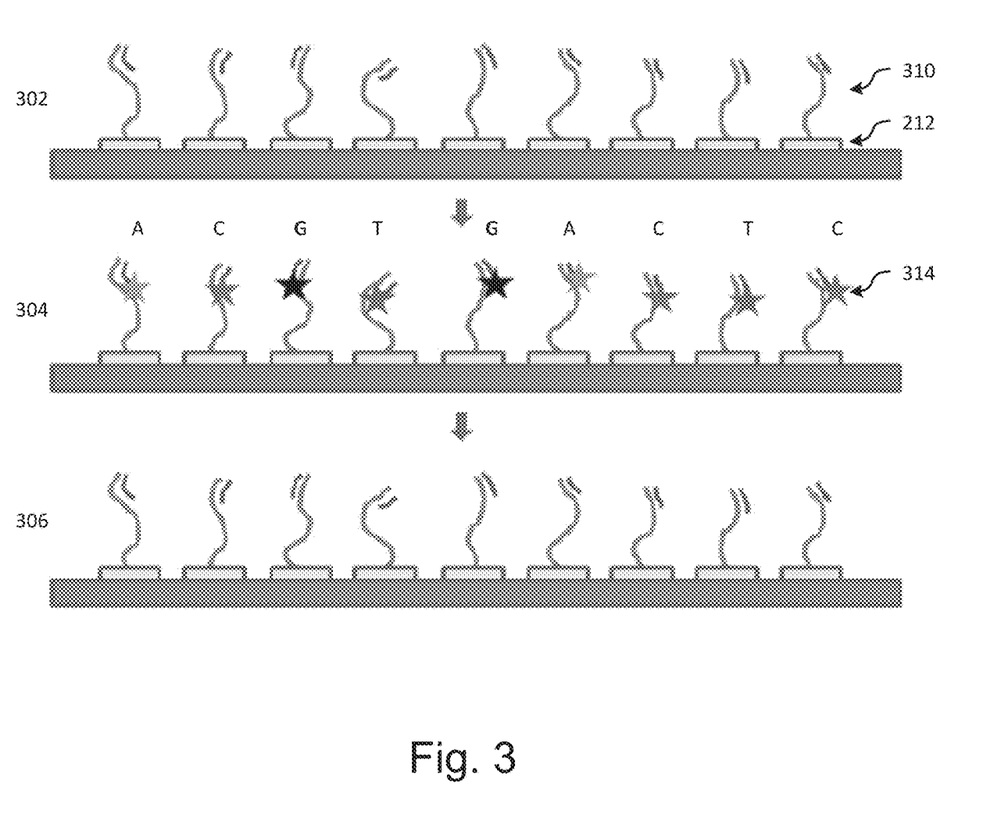
FIG. 3 illustrates an example of a side view of a row of the container illustrated in FIG. 2 in the context of a particular stochastic photo-switching chemistry.
Figure 4:
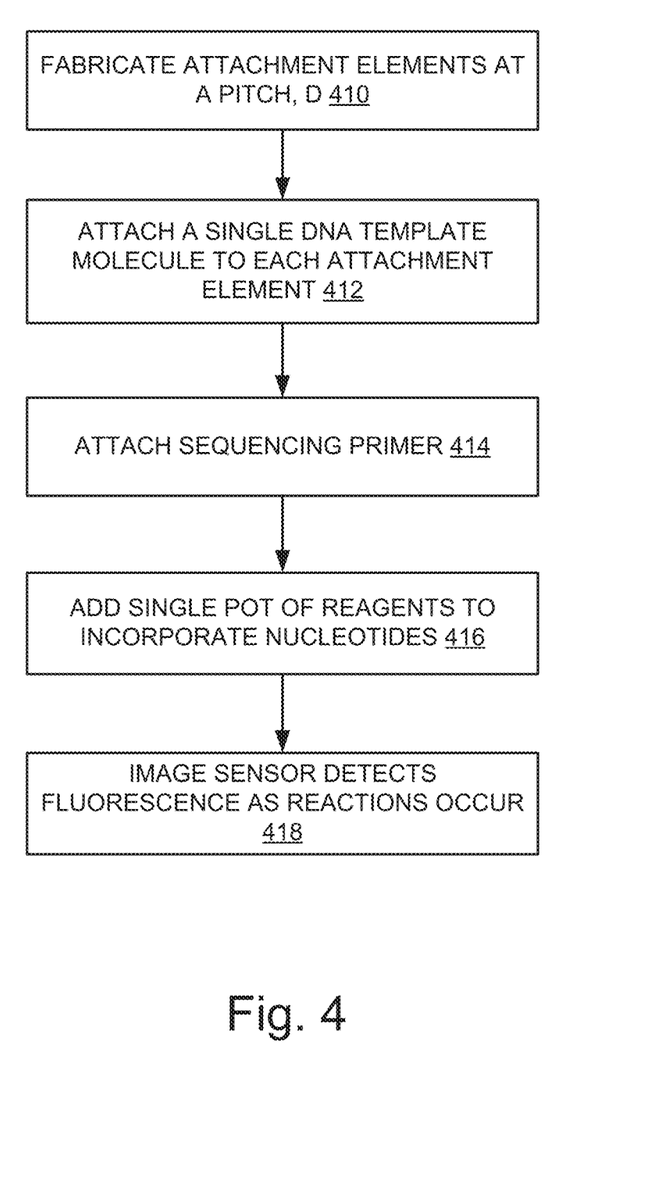
FIG. 4 illustrates an example process for super-resolution sequencing.

FIG. 3 illustrates an example of a side view of a row of the container illustrated in FIG. 2. FIG. 4 illustrates an example process for sequencing. At operation 410, the sample container is fabricated and provided with attachment elements, or anchors (e.g., attachment elements 212). The attachment elements are provided having a pitch, d. In some applications, the pitch, d, can be the same in both directions, while in other applications it can vary. For example, the pitch, d, in some applications can be less than about 20 nm. As another example, in some applications the pitch can range in dimension from about 2 nm to about 20 nm. In some applications the pitch can be greater than or less than this range of dimensions. In further examples, the pitch can be reduced to the smallest dimension possible without the individual molecules being affected by physical interactions between them such as, for example, charge-charge interactions between the molecules.

In this example, single-pot real-time chemistry is used for sequencing. Individual DNA template molecules 310 are provided. These may be anchored to the attachment elements 212 (e.g., one per attachment element 212) as shown in FIG. 3 at 302. Accordingly, at operation 412, a single DNA template molecule 310 is attached to each attachment element. In one example, to ensure that only one molecule exists per patterned attachment point 212, the attachment points may be fabricated at a very small scale, approaching the molecular scale (>~20 nm). In this way, through steric hindrance this can help to ensure that only one DNA molecule attaches at each location. Sequencing single molecules can allow a high density of clusters, as the clusters can be the smallest possible size. This allows the effect of cluster size to be removed as a factor for determining the minimum pitch. Also, with single-molecule sequencing, there is little or no risk of "pad-hopping", whereby a cluster grows across the interstitial space and creates a neighboring duplicate. This hopping is a consequence of the amplification process and generally will not occur when there is no amplification. Also, because there is no amplification, this may also save not only time, but also the cost of the reagents required. By performing single-molecule sequencing, it is then possible to account for phasing errors in each molecule during sequencing.

At operations 414 and 416, a sequencing primer is attached and single-pot reagents are added. This is shown in FIG. 3 at 304. These reagents 314 can include a set of four nucleotides that have a 5' diphosphate quencher molecule and 3' phosphate block, with a label moiety (e.g., dye molecule).

As used herein, the term "nucleic acid" can be used refer to at least two nucleotide analog monomers linked together. A nucleic acid can contain phosphodiester bonds, however, in some applications, a nucleic acid can be an analog having other types of backbones, comprising, for example, phosphoramide, phosphorothioate, phosphorodithioate, peptide nucleic acid backbones and linkages, positive backbones, or non-ionic backbones. A nucleic acid can include a pentose moiety such as ribose (present in naturally occurring RNA), deoxy-ribose (present in naturally occurring DNA) or dideoxy ribose. In some applications a nucleic acid can have a non-pentose moiety or carbocyclic sugar instead of a ribose or deoxyribose moiety. A nucleic acid can have one or more different base moieties including, but not limited to, adenine (A), guanine (G), thymine (T), uracil (U), cytosine (C), inosine, xanthanine, hypoxanthanine, isocytosine, isoguanine, nitropyrrole (including 3-nitropyrrole) and/or nitroindole (including 5-nitroindole). Nucleic acids may be single stranded or double stranded, as specified, or contain portions of both double stranded and single stranded sequence. The nucleic acid may be DNA (e.g. genomic DNA or cDNA), RNA or a hybrid.

As used herein, the term "nucleotide analog" is intended to include natural nucleotides, non-natural nucleotides, ribonucleotides, deoxyribonucleotides, dideoxyribonucleotides and other molecules known as nucleotides. The term can be used to refer to a monomer unit that is present in a polymer, for example to identify a subunit present in a DNA or RNA strand. The term can also be used to refer to a monomeric molecule that is not necessarily present in a polymer, for example, a molecule that is capable of being incorporated into a polynucleotide in a template dependent manner by a polymerase. The term can refer to a nucleoside unit having, for example, 0, 1, 2, 3, 4, 5 or more phosphates on the 5' carbon. A nucleotide analog can have a base moiety including, but not limited to, adenine (A), guanine (G), thymine (T), uracil (U), cytosine (C), inosine, xanthanine, hypoxanthanine, isocytosine, isoguanine, nitropyrrole (including 3-nitropyrrole) and/or nitroindole (including 5-nitroindole). Example natural nucleotides include, without limitation, ATP, UTP, CTP, GTP, ADP, UDP, CDP, GDP, AMP, UMP, CMP, GMP, dATP, dTTP, dCTP, dGTP, dADP, dTDP, dCDP, dGDP, dAMP, dTMP, dCMP, and dGMP.

Non-natural nucleotides include those that are not present in a natural biological system. A non-natural nucleotide can be incapable of being further extended after being incorporated into a polynucleotide. Examples include, nucleotide analogs having a reversible or non-reversible blocking moiety. A natural or non-natural nucleotide can be capable of being further extended after being incorporated into a polynucleotide. Examples include, nucleotide analogs having a 3' hydroxyl. In some applications, the nucleotide analog(s) will not include a reversible blocking moiety, or the nucleotide analog(s) will not include a non-reversible blocking moiety or the nucleotide analog(s) will not include any blocking moiety at all.

As used herein, the term "blocking moiety," when used in reference to a nucleotide analog, means a part of the nucleotide analog that inhibits or prevents the nucleotide analog from forming a covalent linkage to a second nucleotide analog. For example, in the case of nucleotide analogs having a pentose moiety, a blocking moiety can prevent formation of a phosphodiester bond between the 3' oxygen of the nucleotide and the 5' phosphate of the second nucleotide. The blocking moiety can be part of a nucleotide that is a monomer unit present in a nucleic acid polymer or the blocking moiety can be a part of a free nucleotide analog (e.g. a nucleotide triphosphate). The blocking moiety that is part of a nucleotide analog can be reversible, such that the blocking moiety can be modified to render the nucleotide analog capable of forming a covalent linkage to a second nucleotide analog. Particularly useful reversible blocking moieties are phosphates, phosphodiesters, phosphotriesters, phosphorothioate esters, and carbon esters. Further examples of reversible blocking moieties that can be used are set forth below and in references incorporated by reference herein as set forth below. In particular applications, a blocking moiety, such as a reversible blocking moiety, can be attached to the 3' position or 2' position of a pentose moiety of a nucleotide analog.

As used herein, the term "label moiety," when used in reference to a nucleotide analog, means a part of the nucleotide analog that provides a distinguishable characteristic that is not otherwise manifest in the nucleotide analog. The distinguishable characteristic can be, for example, an optical signal such as absorbance of radiation, fluorescence emission, luminescence emission, fluorescence lifetime, fluorescence polarization, or the like; binding affinity for a ligand or receptor; magnetic properties; electrical properties; charge; mass; radioactivity or the like. Example label moieties include, without limitation, a fluorophore, luminophore, chromophore, radioactive isotope, mass label, charge label, spin label, receptor, ligand, or the like. The label moiety can be part of a nucleotide that is a monomer unit present in a nucleic acid polymer or the label moiety can be a part of a free nucleotide analog (e.g. a nucleotide triphosphate).

As used herein, the term "label-modifier moiety," when used in reference to a nucleotide analog having a label moiety, means a part of the nucleotide analog that changes a distinguishable characteristic of the label moiety. Typically, the change in the distinguishable characteristic is manifest in the presence of the label-modifier moiety but not in the absence of the label-modifier moiety. For example, a label-modifier moiety can be a quencher that reduces fluorescence or luminescence emission from a label. In another example, a label-modifier moiety can be a Forster resonance energy transfer (FRET) donor or acceptor that changes the intensity or wavelength of fluorescence or luminescence emission detected from the label. The label-modifier moiety can be part of a nucleotide that is a monomer unit present in a nucleic acid polymer or the label-modifier moiety can be a part of a monomeric nucleotide analog (e.g. a nucleotide triphosphate).

As used herein, the term "deblocking agent" means a catalyst, enzyme, reagent or other substance that is capable of modifying or removing a blocking moiety. In particular applications, a deblocking agent can have specificity for a blocking moiety that is part of a nucleotide that is a monomer unit present in a nucleic acid polymer. As such the deblocking agent may selectively remove a blocking moiety from a nucleotide analog that is present in a nucleic acid compared to a blocking moiety that is part of a monomeric nucleotide analog (e.g. a nucleotide triphosphate). Alternatively or additionally, a deblocking agent can selectively remove a blocking moiety from a nucleotide analog that is present in a double stranded nucleic acid compared to a blocking moiety that is part of a monomeric nucleotide analog (e.g. a nucleotide triphosphate) or part of a nucleotide analog that is a monomer in a single stranded nucleic acid. Accordingly, in some applications the deblocking agent can have little or no ability to remove a blocking moiety from a monomeric nucleotide analog (e.g. a nucleotide triphosphate) or from nucleotide analog that is a monomer in a single stranded nucleic acid. Example deblocking agents include, but are not limited to, an enzyme, such as a phosphoesterase, phosphodiesterase, phosphotriesterase, esterase, alkyl transferase or methyl transferase; or a chemical reagent.

As used herein, reference to "selectively" manipulating (e.g., to "selectively" remove) a first thing compared to second thing is intended to mean that the manipulation has a greater effect on the first thing compared to the effect on the second thing. The manipulation need not have an effect on the second thing. The manipulation can have an effect on the first thing that is at least 1%, 5%, 10%, 25%, 50%, 75%, 90%, 95%, or 99% greater than the effect on the second thing. The manipulation can have an effect on the first thing that is at least 2 fold, 3 fold, 4 fold, 5 fold, 10 fold, 100 fold, $1\times10^3$ fold, $1\times10^4$ fold or $1\times10^6$ fold higher than the effect on the second thing. The manipulation can include, for example, modifying, contacting, treating, changing, cleaving (e.g. of a chemical bond), photo-chemically cleaving (e.g. of a chemical bond), forming (e.g. of a chemical bond), photo-chemically forming (e.g. of a chemical bond), covalently modifying, non-covalently modifying, destroying, photo-ablating, removing, synthesizing, polymerizing, photo-polymerizing, amplifying (e.g. of a nucleic acid), copying (e.g. of a nucleic acid), extending (e.g. of a nucleic acid), ligating (e.g. of a nucleic acid), or other manipulation set forth herein or otherwise known in the art. As used herein, the term "transient," when used in reference to a species in a reaction or reaction cycle, means the species is present only temporarily during the course of the reaction or reaction cycle. A transient species can be present, for example, for a time period that is no more than about 10 minutes, 1 minute, 30 seconds, 10 seconds, 1 second, 100 milliseconds, 10 milliseconds, 1 millisecond, 100 nanoseconds, 10 nanoseconds, or 1 nanosecond. In particular applications, the transient species is present for a temporary time period that is sufficient to allow detection of the transient species. For example, additionally or alternatively to the example maximum times periods set forth above, a transient species may be present for at least 1 minute, 30 seconds, 10 seconds, 1 second, 100 milliseconds, 10 milliseconds, 1 millisecond, 100 nanoseconds, 10 nanoseconds, 1 nanosecond or 1 picosecond.

As used herein, the term "reaction cycle," when used in reference to a reactant and product, means a sequence of two or more reactions that convert the reactant to at least one transient species and then convert the at least one transient species to the product. The reaction cycle can be repeated, for example, such that the product serves as a reactant in the same sequence of reactions. For example, a nucleic acid primer can be extended by a single nucleotide in a first reaction cycle to produce a primer extension product (having a single nucleotide added to the original primer) and then the primer extension product can be extended again in a second reaction cycle to produce a primer extension product (having two nucleotides added to the original primer). The repetition of the cycle can use slightly different reactants, for example, different nucleotide analogs can be added in sequential cycles of primer extension. However, a reaction cycle need not be repeated. A nucleic acid reaction cycle can, for example, result in the addition of a single nucleotide to a primer (e.g. in a polymerase catalyzed reaction) or in the addition of a single oligonucleotide to a primer (e.g. in a ligase catalyzed reaction).

Labels that are optically detectable are particularly useful. Examples include chromophores, luminophores and fluorophores. Fluorophores are particularly useful and include, for example, fluorescent nanocrystals; quantum dots, fluorescein, rhodamine, tetramethylrhodamine, eosin, erythrosin, coumarin, methyl-coumarins, pyrene, Malacite green, Cy3, Cy5, stilbene, Lucifer Yellow, Cascade Blue, Texas Red, Alexa dyes, SETA dyes, Atto dyes, phycoerythin, bodipy, and analogs thereof. Useful optical probes are described in Haugland, Molecular Probes Handbook, (Eugene, Oreg.) 6th Edition; The Synthegen catalog (Houston, Tex.), Lakowicz, Principles of Fluorescence Spectroscopy, 2nd Ed., Plenum Press New York (1999), or WO 98/59066; WO 91/06678 or US Pat. Appl. Publ. No. 2010/0092957 A1, each of which is incorporated herein by reference. Optical labels provide an advantage of rapid, relatively non-invasive detection thereby allowing real time monitoring of a cyclic reaction.

Other labels, some of which are non-optical labels, can be used in various applications of the methods and compositions set forth herein. Examples include, without limitation, an isotopic label such as a naturally non-abundant radioactive or heavy isotope; magnetic substance; electron-rich material such as a metal; electrochemiluminescent label such as $Ru(bpy)_3 2+$; or moiety that can be detected based on a nuclear magnetic, paramagnetic, electrical, charge to mass, or thermal characteristic. Labels can also include magnetic particles or optically encoded nanoparticles. Such labels can be detected using appropriate methods known to those skilled in the art. For example, a charged label can be detected using an electrical detector such as those used in commercially available sequencing systems from Ion Torrent (Guilford, Conn., a Life Technologies subsidiary) or detection systems described in US Pat. App. Publ. Nos. 2009/0026082 A1; 2009/0127589 A1; 2010/0137143 A1; and 2010/0282617 A1, each of which is incorporated herein by reference. It will be understood that for some applications a nucleotide analog need not have a label.

Another type of label that can be useful is a secondary label that is indirectly detected, for example, via interaction with a primary label, binding to a receptor or conversion to a detectable product by an enzyme catalyst or other substance. An example secondary label is a ligand such as biotin or analogs thereof that can be detected via binding to a receptor such as avidin, streptavidin or analogs thereof. Other useful ligands are epitopes that can bind to receptors such as antibodies or active fragments thereof, and carbohydrates that can bind to receptors such as lectins. The receptors can be labeled, for example, with an optical label, to allow them to be detected. In particular applications, the ligand can be attached to a nucleotide analog in a way that reduces or prevents affinity to a receptor. Release of the ligand can then be detected based on affinity of the ligand for its respective receptor when detached from the nucleotide analog. The ligand can further be attached to a blocking moiety or may itself function as a blocking moiety, as set forth above more generally for label moieties. Thus, removal of the ligand from a nucleotide analog can function to deblock the nucleotide analog and to provide a detectable event.

Another example secondary label is pyrophosphate or analogs thereof. Pyrophosphate can be detected by solid-phase chelators and/or electronic biosensors. In some applications, pyrophosphate can be detected by a cascade of enzymes that converts pyrophosphate to ATP and then to chemiluminescence. Example enzyme cascades include those typically used in pyrosequencing and/or described in US Pat App. Publ. No. 2005/0244870 A1, which is incorporated herein by reference. In some applications, use of an enzyme cascade detection system that produces ATP may require use of an Adenine nucleotide analog, such as ATPγS, that is incorporated into a primer by polymerase but does not cause a background signal that competes with the pyrophosphate signal. In particular applications, pyrophosphate or an analog thereof can be attached to a nucleotide analog at a position other than the 5' position where a triphosphate resides. This nucleotide analog can produce two pyrophosphate-induced signals in an appropriate detection system, one due to the release of pyrophosphate from the 5' position (due to polymerase activity) and a second due to release from the other position, for example, by a deblocking agent. Production of two pyrophosphate-induced signals can provide an advantage of increased signal to noise in a detection step or increased accuracy in evaluating sequencing data. A particularly useful analog of pyrophosphate, when present on a nucleotide analog, will be charge-neutral at one or more of the oxygen moieties that are typically negatively charged in pyrophosphate. In one example the pyrophosphate analog can have no charged oxygen atoms. Charge neutrality may favor interactions with some polymerase species. The pyrophosphate analog, once released, can be converted to a form for interaction with enzymes in a detection cascade if appropriate or otherwise desired.

A label moiety that is used in a method or composition set forth herein can be an intrinsic label (i.e. an endogenous label) that is present in a naturally occurring molecule being detected, such as a proton or pyrophosphate that is released from a nucleotide analog upon incorporation into an extended primer. Pyrophosphate release can be detected using a pyrosequencing or similar technique, examples of which are commercially available from 454 Life Sciences (Branford, Conn., a Roche Company) or described in US Pat App. Publ. No. 2005/0244870 A1, which is incorporated herein by reference. Example systems for detecting primer extension based on proton release include those that are commercially available from Ion Torrent (Guilford, Conn., a Life Technologies subsidiary) or described in US Pat. App. Publ. Nos. 2009/0026082 A1; 2009/0127589 A1; 2010/0137143 A1; and 2010/0282617 A1, each of which is incorporated herein by reference. Alternatively or additionally to detection of an intrinsic label, one can detect a label that is exogenous to a natural nucleotide analog. Thus, in some applications solely exogenous probes are detected such that endogenous probes are not detected, in other applications solely endogenous probes are detected such that exogenous probes are not detected and in some applications a combination of exogenous and endogenous probes are detected.

In some applications a label moiety that is detectable under the conditions being used is not necessary or not desirable. Thus, a nucleotide analog that is present in a reaction mixture or used in a reaction set forth herein may lack a particular detectable label moiety when in a monomeric form and when incorporated into an extended primer. The nucleotide analog may nonetheless include a blocking moiety. In such applications, detection may not be carried out at all.

In addition to a label moiety, a nucleotide analog can further include a label-modifier moiety. A label-modifier moiety can function to modify a signal produced by the label moiety. In some applications, a signal that is produced by the label moiety in the presence of the label-modifier moiety can be distinguished from a signal that is produced by the label moiety in the absence of the label-modifier moiety. For example, the label moiety and label-modifier moiety can be a Forster resonance energy transfer (FRET) donor-acceptor pair. As such, a change in the wavelength of apparent fluorescence emission from a nucleotide analog can be detected and will be indicative of the presence or absence of the label-modifier moiety. Example fluorophores that can be used as members of FRET pairs include, but are not limited to, fluorescent nanocrystals; quantum dots; d-Rhodamine acceptor dyes including dichloro[R110], dichloro[R6G], dichloro[TAMRA], dichloro[ROX] or the like; fluorescein donor dye including fluorescein, 6-FAM, or the like; Cyanine dyes such as Cy3B; Alexa dyes, SETA dyes, Atto dyes such as Atto 647N which forms a FRET pair with Cy3B and the like.

In another example, the intensity of a signal from a label moiety that occurs in the presence of the label-modifier moiety can be distinguished from the intensity of signal that is produced in the absence of the label-modifier moiety. For example, the label can be a fluorophore and the label-modifier moiety can be a quencher such that absence of the label-modifier moiety can be detected as an apparent increase of fluorescence emission from the nucleotide analog. Example quenchers include, but are not limited to, DACYL(4-(4'-dimethylaminophenylazo)benzoic acid), Black Hole Quenchers (Biosearch Technologies, Novato, Calif.), Qxl quenchers (Anaspec, Freemont, Calif.), Iowa black quenchers, DABCYL, BHQ1, BHQ2, QSY7, QSY9, QSY21, QSY35, BHQO, BHQ1, BHQ2, QXL680, ATTO540Q, ATTO580Q, ATTO612Q, DYQ660, DYQ661 and IR Dye QC-1 quenchers.

Figure 5:
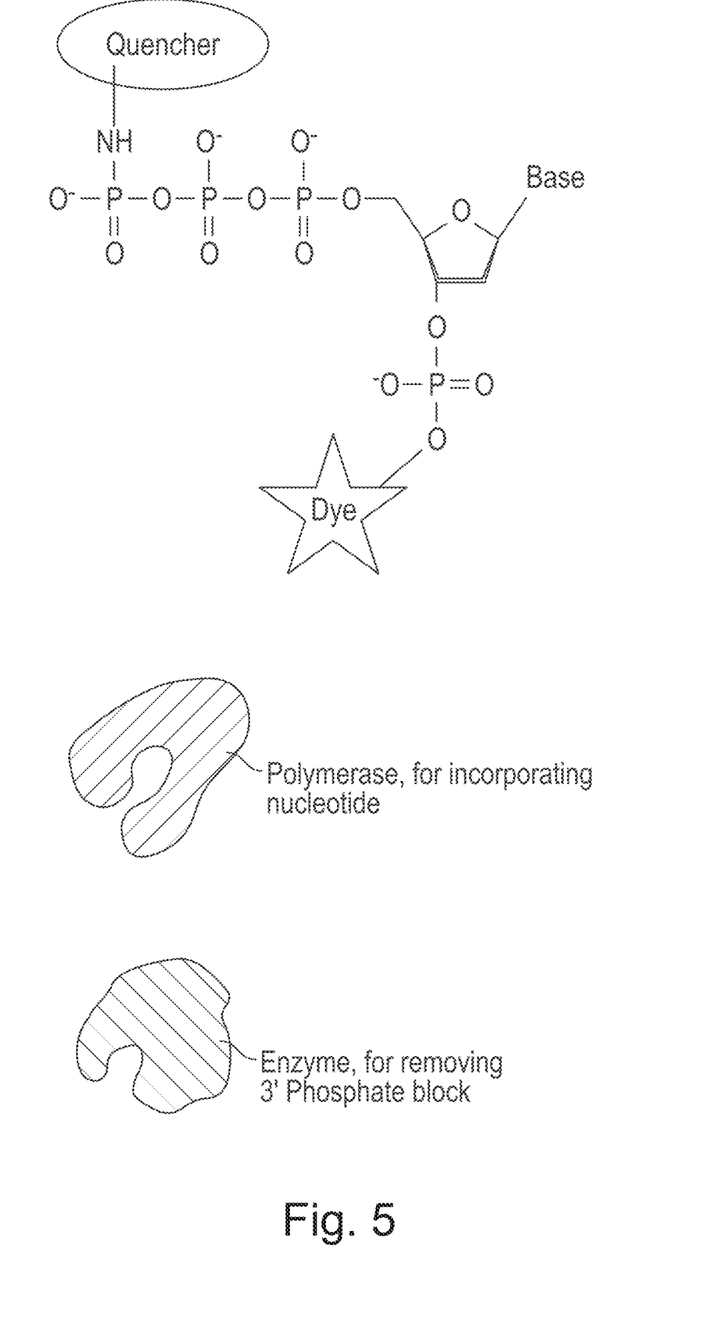
FIG. 5 illustrates an example of ratchet biochemistry components that can be used in the super-resolution sequencing examples described herein.

An example of the ratchet biochemistry components is shown in FIG. 5. This example includes a 3' phosphate dye and a 5' tri-phosphate quencher. This example kit also includes a polymerase that can incorporate the nucleotides, and also a dsDNA specific enzyme that will cleave the 3' phosphate block but only from nucleotides that have been incorporated.

Any of a variety of polymerases can be used in a method or composition set forth herein including, for example, protein-based enzymes isolated from biological systems and functional variants thereof. Reference to a particular polymerase, such as those exemplified below, will be understood to include functional variants thereof unless indicated otherwise. A particularly useful function of a polymerase is to catalyze the polymerization of a nucleic acid strand using an existing nucleic acid as a template. Other functions that are useful are described elsewhere herein. Examples of useful polymerases include DNA polymerases and RNA polymerases. Particularly useful polymerases include Pol217 and Pol427 as set forth in the Examples section below and other polymerase described in US 2006/0240439 A1, which is incorporated herein by reference.

A polymerase having an intrinsic 3' to 5' proofreading exonuclease activity can be useful for some applications. Polymerases that substantially lack 3' to 5' proofreading exonuclease activity are also useful in some applications, for example, in most sequencing applications. Absence of exonuclease activity can be a wild type characteristic or a characteristic imparted by a variant or engineered polymerase structure. For example, exo minus Klenow fragment is a mutated version of Klenow fragment that lacks 3' to 5' proofreading exonuclease activity.

Polymerases can be characterized according to their rate of dissociation from nucleic acids. In particular applications it is desirable to use a polymerase that has a relatively high dissociation rate. This can be useful for example, in applications where dissociation of the polymerase allows a deblocking step to proceed. For example, an enzyme when used as a deblocking agent may be sterically blocked by a polymerase such that the enzyme is prevented from removing a blocking moiety from an extended primer. In such a case, the lifetime of the extended primer having the blocking moiety can be influenced by the dissociation rate of the polymerase. The dissociation rate is an activity of a polymerase that can be adjusted to tune reaction rates in methods set forth herein.

Depending on the example that is to be used, a polymerase can be either thermophilic or heat inactivated. Thermophilic polymerases are typically useful for high temperature conditions or in thermocycling conditions such as those employed for polymerase chain reaction (PCR) techniques. Examples of thermophilic polymerases include, but are not limited to 9° N DNA Polymerase, Taq DNA polymerase, Phusion® DNA polymerase, Pfu DNA polymerase, RB69 DNA polymerase, KOD DNA polymerase, and VentR® DNA polymerase. Most polymerases isolated from non-thermophilic organisms are heat inactivated. Examples are DNA polymerases from phage. It will be understood that polymerases from any of a variety of sources can be modified to increase or decrease their tolerance to high temperature conditions.

Figure 6:
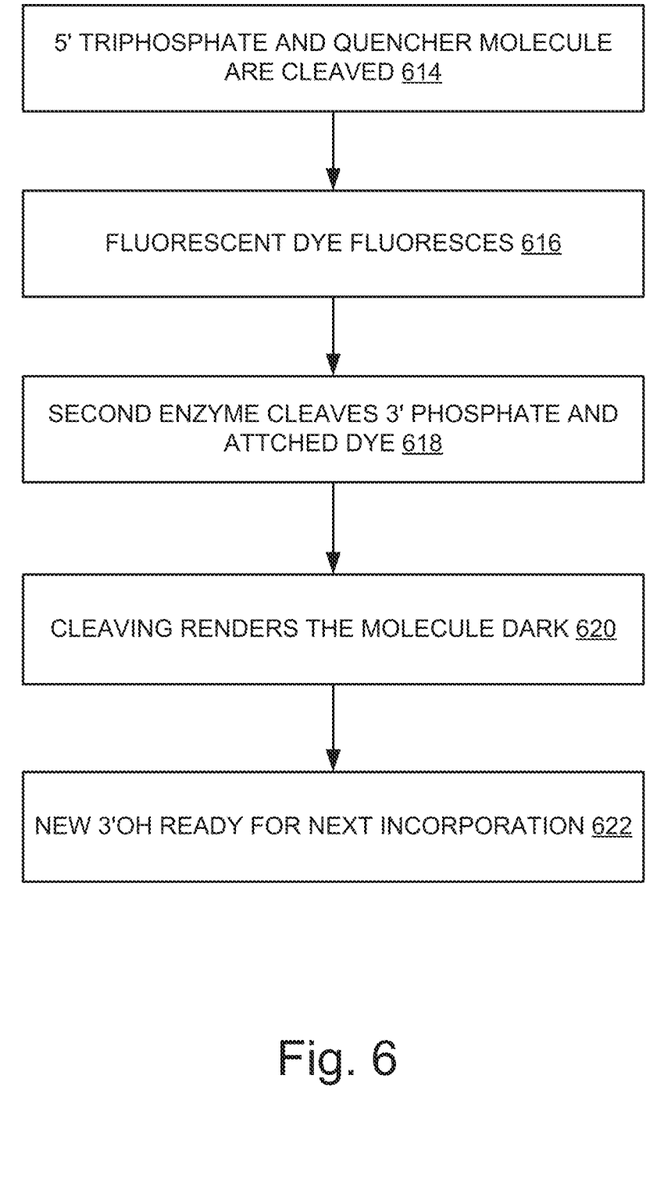
FIG. 6 illustrates an example of the chemical process upon the incorporation of the nucleotides

FIG. 6 illustrates an example of a chemical process upon the incorporation of the nucleotides. Referring now to FIG. 6, at 614, as a nucleotide is incorporated the 5' triphosphate is cleaved. Because the Quencher molecule is attached, this Quencher molecule is also cleaved. As a result, the fluorescent dye is no longer quenched and can emit fluorescence as shown in 616. At 618, now that the nucleotide is incorporated in dsDNA the second enzyme is then able to cleave the 3' phosphate, along with the attached dye. This is shown in FIG. 3 at 306. This renders the molecule dark again as shown at 620, and generates a new 3' OH, ready for the next incorporation (shown at 622). There is some time that passes between the incorporation event occurring and the fluorophore switching on, and the removal of phosphate block causing the fluorophore to diffuse away (out of the excitation volume) and switching off.

As another further example, in some applications, the sequencing process can include providing a mixture including an enzyme capable of coupling nucleotides, a deblocking agent, a nucleic acid bound to a strand of nucleotides having a sequence complimentary to the nucleotide sequences anchored to the solid support, and more than one nucleotide analog including a base with a label moiety and corresponding quencher moiety bound thereto. The label moieties may be correlated with a specific base moiety. The process may further allow sequential addition of a plurality of the nucleotide analogs to the nucleic acid to proceed via several reaction cycles in the mixture while concurrently imaging (e.g., operation 418, below) the label moieties within the array. In some applications, each reaction cycle may include: (i) the polymerase adding a nucleotide analog to the nucleic acid by cleaving the quencher moiety and forming a transient nucleic acid species comprising the label moiety; and (ii) the deblocking agent modifying the transient nucleic acid species to remove the label moiety. In various applications, the several reaction cycles may include at least 100 reaction cycles, whereby the nucleic acid is extended by addition of at least 100 nucleotide analogs. The enzyme capable of coupling nucleotides may include a polymerase, a myosin or a kinase. The nucleotide analog may include a pentose moiety having a 3' carbon and the label moiety may be attached to the nucleotide at the 3' carbon. In another example, the nucleotide analog may include a triphosphate moiety and the quencher moiety may be attached to the triphosphate moiety.

In some applications, the deblocking agent may include a phosphoesterase enzyme (e.g., phosphodiesterase, phosphotriesterase), which may be included to selectively remove a phosphodiester moiety or the phosphotriester moiety from the transient nucleic acid species. The phosphoesterase may be selected from the group consisting of Endonuclease IV and AP endonuclease. The transient nucleic acid species may be present for at least 1 millisecond before the deblocking agent modifies the transient nucleic acid species to remove the label moiety. As a further example, the transient nucleic acid species may be present for no more than 30 seconds before the deblocking agent modifies the transient nucleic acid species to remove the label moiety.

Returning now to FIG. 4, at operation 418 an imaging system of the sequencer detects the intensity of the signal in each of the four channels (ACGT), and the fluorescence of the dye is manifested as an increase in signal corresponding to the base that has been incorporated. Accordingly, the fluorescence is detected by an image sensor in the imaging system (e.g., camera system 140 in the example imaging system of FIG. 1), and the images can be recorded. The imaging and recording system can image and record multiple channels at the same time (e.g., one channel for each base), and each channel can image and record the on and off sequences for that channel at all of the locations within its field of view. Because of the stochastic nature of the process, all of the molecules within the field of view of the imaging system can be activated at the same time and the reactions occurring recorded in each channel simultaneously for all of the molecules within the field of view.

In other words, in various applications the sequencing is occurring by incorporating the correct nucleotides by polymerase for a given molecule, while other incorporation events are going on around it randomly and the imaging can be running in real time to detect the reactions in each of the molecules as they are occurring. As noted, the imaging can be arranged to observe the four different color channels, one for each base, and each channel can detect and record its florescence turning on and off.

Figure 7:
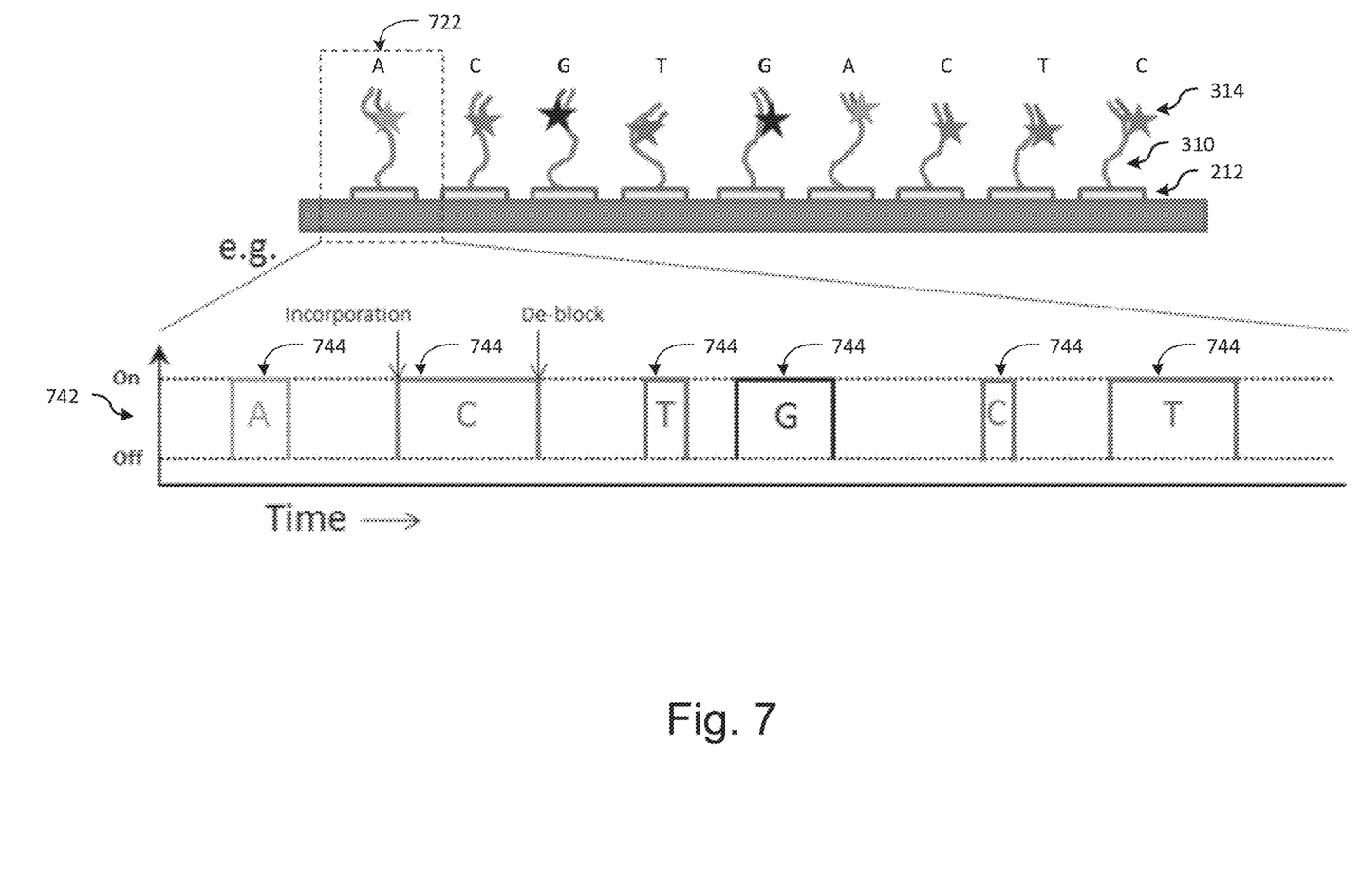
FIG. 7 illustrates an example of the process of super-resolution imaging using the above-described chemical process.

FIG. 7 illustrates an example of the process of super-resolution imaging using the above-described chemical process. This shows an example of the 'on' and 'off' events 742 as nucleotide incorporation and deblocking events occur over time for a single molecule 722. The time traces of the on/off state for each molecule to determine the sequence of that molecule. In the illustrated example, 'on' states 744 are illustrated for molecule 722 in a sequence of ACTGCT.

In various applications, the incorporation and deblocking events are stochastic and not synchronized between molecules. Therefore, statistically, 'on' events for a given base for a given molecule at a given location may occur at different times from 'on' events for that base for other molecules at adjacent or surrounding locations. Accordingly, for each channel, there is a statistical probability that for each channel an on-events for that channel are sufficiently spatio-temporally separated such that they are resolvable as separate events by the imaging system despite the fact that the molecules are spaced at a pitch smaller than would otherwise be allowed by Abbe's limit. This randomly generated spatio-temporal separation between 'on' events for a given base provides a greater effective pitch between events than the actual well spacing, making the 'on' events resolvable by the optics of the imaging system. An example of this is shown at 304 in FIG. 3. In this example, each of the molecules in this center row is currently exhibiting and on an event for a base that is different from its adjacent molecules. In this example, the molecules from left to right are exhibiting on events for the bases A, C, G, T, G, A, C, T and C. The nearest occurrences of an on event for the same bases are the two C events on the right-hand side of the road, and the 2 G events toward the center of the row. In each case, these are spaced 2d, or twice the average pitch of the attachment elements 212.

Because the photo-switching is stochastic, there may be occasions when two or more molecules closer together than otherwise allowed by Abbes' limit (e.g., 2 adjacent molecules) are switched on for the same base at the same time. In this case, these molecules might not be resolved. This possibility can be mitigated by controlling the switching rates to render these coincident adjacent events to be rare. For example, the concentrations of nucleotides and enzyme can be adjusted to allow the dyes to remain 'on' for a sufficient time to identify the base. Also, these concentrations can be selected so that not only is the 'on' time sufficient, but also so the 'off' time is long enough so that there are few or no similar 'on' events occurring in close proximity to one another. For example, in one application, the on and off times are selected so that the probability of a dye being on for a given location at the same time a dye is on at an immediately adjacent location is less than or equal to 0.5%. In another application, the on and off times are selected so that the probability of a dye being on for a given location at the same time a dye is on at an immediately adjacent location is greater than or equal to 0.5%. In other applications, the on and off times are selected so that the probability of a dye being on for a given location at the same time a dye is on at an immediately adjacent location is in the range of 0.1% to 0.5%. In other applications, the on and off times are selected so that the probability of a dye being on for a given location at the same time a dye is on at an immediately adjacent location is in the range of 0.1% to 0.8%. In another application, the on and off times are selected so that this adjacency probability is lower than an acceptable error rate in the given sequencing application in which it is applied.

There may also be other ways to address the situation in which 'on' events for a given channel occur too close together to be resolved by the imaging system. In one example, the system can detect an illumination intensity greater than an average or baseline illumination intensity, or other threshold, indicating that illumination events occurred for a given base for two or more molecules closer together than Abbe's limit. Likewise, the spot size or spot shape may also be used to determine a situation in which two or more molecules closer together than Abbe's limit are exhibiting and on event at the same time for a given base. Accordingly, comparing an illumination event to an illumination intensity threshold, spot size threshold, or both, can be a technique used to allow the system to determine whether two adjacent molecules exhibited an on event at the same time for the same base. This may allow for increased tolerance of the system to these adjacencies, which may in turn allow the on and off times to be selected to permit a higher adjacency probability than might otherwise be tolerated without either or both of these threshold determinations. Further examples may also be implemented such that once aligned to a reference genome, apparent "deletion" errors may be resolved by observing which bases occurred in adjacent reads at that same moment in time. For example a deletion that should have been a "C" coincides with a correctly called "C" in an adjacent site.

Processes described herein provide a way to achieve photo-switching, by enzymatic cycling of fluorophores between dark and light states. This cycling could be through one of many enzymes, e.g. polymerase, such as those described herein. It could also be through other enzymes that turn over nucleotides (e.g. Adenosine triphosphate (ATP) by myosins, or kinesins), or any multi-partite substrate in which the enzymatic process separates the parts (e.g. a quencher from a fluorescent dye). These could be quenched at the 5' end (with a 3'-dye label) similar to the process described above, and therefore when they are hydrolyzed they fluoresce, and then return to darkness when the ADP products are released. Another example can be an enzymatic processes that joins non-fluorescent molecules together in a reaction that yields a functional fluorophore. This fluorophore may then get broken down again by application of an orthogonal chemistry.

In further applications, the systems and methods described herein can use alternative techniques to the above-described ratchet chemistry process to achieve stochastic photo-switching of molecules in simultaneous adjacent reactions. For example, the photo-switching techniques of STORM (STochastic Optical Reconstruction Microscopy) or DNA Points Accumulation for Imaging in Nanoscale Topography (DNA-PAINT) techniques for photo-switching of the fluorophores can be used as described above, with similar effects as achieved by the chemistry described above. Accordingly, the on and off switching may be achieved in a number of different ways, such as, for example, direct switching driven by photochemical reactions (dSTORM), or transient DNA hybridization of DNA labels (DNA-PAINT). Various reagents could be created, with e.g. antibodies against specific targets, coupled to such enzymatic moieties for driving the photo-switching.

STORM, for example, originally overcame Abbe's limit by having fluorophores that switch on and off in spatially remote locations, and sequential frames of these events are recorded as the locations change. In any given frame, only a small fraction of the fluorophores would be switched on, and these are sufficiently separated beyond Abbe's limit. However, this is a sequential process in which the fluorophores are energized, recorded and erased and the process then must be repeated for all locations until all molecules are captured. This would require the acquisition of many successive frames so that all molecules can be recorded and a complete image of the object obtained. However, applications of the processes described herein enable the reactions for all of the molecules within the field of view to occur at the same time (instead of energizing, erasing and repeating for sufficiently separated molecules) and imaging the process in real-time as it occurs. This takes advantage of the stochastic nature of the reactions so that they are statistically not occurring next to one another frequently and they can be captured by the multiple channels (e.g., one for each base) of the imaging system in real-time.

While various examples of the disclosed technology have been described above, it should be understood that they have been presented by way of example only, and not of limitation. Likewise, the various diagrams may depict an example architectural or other configuration for the disclosed technology, which is done to aid in understanding the features and functionality that can be included in the disclosed technology. The disclosed technology is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the technology disclosed herein. Also, a multitude of different constituent module names other than those depicted herein can be applied to the various partitions. Additionally, with regard to flow diagrams, operational descriptions and method claims, the order in which the steps are presented herein shall not mandate that various examples be implemented to perform the recited functionality in the same order unless the context dictates otherwise.

Although the disclosed technology is described above in terms of various example examples and implementations, it should be understood that the various features, aspects and functionality described in one or more of the individual examples are not limited in their applicability to the particular example with which they are described, but instead can be applied, alone or in various combinations, to one or more of the other examples of the disclosed technology, whether or not such examples are described and whether or not such features are presented as being a part of a described example. Thus, the breadth and scope of the technology disclosed herein should not be limited by any of the above-described example examples. It should be appreciated that all combinations of the foregoing concepts (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide example instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. The term comprising is intended herein to be open-ended, including not only the recited elements, but any additional elements as well. Likewise, where this document refers to technologies that would be apparent or known to one of ordinary skill in the art, such technologies encompass those apparent or known to the skilled artisan now or at any time in the future. To the extent applicable, the terms "first," "second," "third," etc. herein are merely employed to show the respective objects described by these terms as separate entities and are not meant to connote a sense of chronological order, unless stated explicitly otherwise herein.

The term "coupled" refers to direct or indirect joining, connecting, fastening, contacting or linking, and may refer to various forms of coupling such as physical, optical, electrical, fluidic, mechanical, chemical, magnetic, electromagnetic, communicative or other coupling, or a combination of the foregoing. Where one form of coupling is specified, this does not imply that other forms of coupling are excluded. For example, one component physically coupled to another component may reference physical attachment of or contact between the two components (directly or indirectly), but does not exclude other forms of coupling between the components such as, for example, a communications link (e.g., an RF or optical link) also communicatively coupling the two components. Likewise, the various terms themselves are not intended to be mutually exclusive. For example, a fluidic coupling, magnetic coupling or a mechanical coupling, among others, may be a form of physical coupling.

The terms "substantially" and "about" used throughout this disclosure, including the claims, are used to describe and account for small fluctuations, such as due to variations in processing. For example, they can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

The presence of broadening words and phrases such as "one or more," "at least," "but not limited to" or other like phrases in some instances shall not be read to mean that the narrower case is intended or required in instances where such broadening phrases may be absent. The use of the term "component" does not imply that the elements or functionality described or claimed as part of the component are all configured in a common package. Indeed, any or all of the various elements of a component, including structural elements, can be combined in a single package or separately maintained and can further be distributed in multiple groupings or packages.

Additionally, the various examples set forth herein are described in terms of example diagrams and other illustrations. As will become apparent to one of ordinary skill in the art after reading this document, the illustrated examples and their various alternatives can be implemented without confinement to the illustrated examples. For example, block diagrams and their accompanying description should not be construed as mandating a particular architecture or configuration.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

We claim:

1. An imaging system comprising:
a sample container comprising a flowcell that comprises a plurality of attachment elements at a plurality of sample locations, wherein a single DNA template molecule is attached to each of the attachment elements, and further wherein an average distance between adjacent attachment elements is less than Abbe's limit; and
an imager positioned to image photo-switching occurring at the plurality of attachment elements by capturing on and off events in a plurality of color channels at the same time as the on and off events are occurring for the attached molecules when a stochastic photo-switching chemistry is applied to all of the attached molecules at the same time causing the attached molecules to fluoresce in the on and off events in up to four different colors.

2. The imaging system of claim 1, wherein each of the plurality of attachment elements on the sample container is within a field of view of the imager used to image the photo-switching such that the capturing of the on and off events occurs at the same time for the attached molecules at the plurality of attachment elements.

3. The imaging system of claim 1, the stochastic photo-switching chemistry applied to all of the attached molecules at the same time comprises a stochastic optical reconstruction microscopy, a DNA Points Accumulation for Imaging in Nanoscale Topography, or a direct stochastic optical reconstruction microscopy stochastic photoswitching chemistry.

4. The imaging system of claim 1, further comprising the stochastic photo switching chemistry, wherein concentrations of reagents for the stochastic photo switching chemistry are sufficient such that the probability that an on event for a given base for a given molecule will occur at the same time as an on event for the same base at a molecule adjacent to the given molecule is less than 0.5%.

5. The imaging system of claim 1, wherein the imaging system is configured to control a rate at which the on and off events occur by adjusting concentrations of nucleotides and enzymes used in the stochastic photo-switching chemistry such that a probability that an on event for a given base for a given molecule will occur at the same time as an on event for the same base at a molecule adjacent to the given molecule is lower than a determined error rate in a sequencing application in which the photo-switching chemistry is applied.

6. The imaging system of claim 5, wherein the plurality of attachment elements include a first attachment element attached to a first DNA template molecule, and a second attachment element attached to a second DNA template molecule.

7. The imaging system of claim 5, further comprising: a fluid delivery device to direct a flow of the nucleotides and the enzymes to the sample container.

8. The imaging system of claim 1, wherein the imaging system is to determine whether an illumination intensity or a spot size of a detected on event in a color channel is greater than a predetermined threshold.

9. The imaging system of claim 1, wherein the average distance between adjacent elements is less than about 20 nm.

10. The imaging system of claim 1, further comprising the stochastic photo-switching chemistry, wherein:
the stochastic photo-switching chemistry comprises a set of nucleotides that have a 5' diphosphate quencher molecule and a 3' phosphate block with a label moiety, a polymerase to incorporate a nucleotide of the set of nucleotides and cleave the 5' diphosphate quencher molecule, and a dsDNA enzyme to cleave the 3' phosphate block with the label moiety from the incorporated nucleotide;

an on event of the on events occurs when the polymerase incorporates the nucleotide of the set of nucleotides and cleaves the 5' diphosphate quencher molecule; and an off event of the off events occurs when the dsDNA enzyme cleaves the 3' phosphate block with the label moiety from the incorporated nucleotide.

* * * * *